US00PP36739P2

(12) United States Plant Patent
Hansen

(10) Patent No.: US PP36,739 P2
(45) Date of Patent: Jun. 10, 2025

(54) ***HELIOPSIS* PLANT NAMED 'Touch of Blush'**

(50) Latin Name: ***Heliopsis helianthoides* (L.) Sweet**
Varietal Denomination: Touch of Blush

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,348

(22) Filed: Nov. 25, 2024

Related U.S. Application Data

(60) Provisional application No. 63/629,781, filed on Nov. 29, 2023.

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 5/02
See application file for complete search history.

*Primary Examiner* — Kent L Bell

(57) ABSTRACT

The new and distinct hardy perennial plant, *Heliopsis* 'Touch of Blush', has dense, rounded, mound habit with extensively-branched, predominately strong upright stems that resist lodging. The foliage is narrowly ovate to broadly lanceolate with green surrounding the veins and near white between the veins and the young foliage shows a reddish-purple blush. Inflorescences have a single layer of overlapping, golden-yellow ray florets and dark-brownish central disk florets. The new plant is freely flowering and begins blooming in early summer and continues for about six weeks. The new plant is useful in the landscape en masse, as an accent, in containers, or as cut flowers.

2 Drawing Sheets

Botanical denomination: *Heliopsis helianthoides* (L.) Sweet.

Variety designation: 'Touch of Blush'.

STATEMENT REGARDING PRIOR DISCLOSURES UNDER 37 CFR 1.77(b)(6)

The first offer for sale was by Walters Gardens, Inc. on Dec. 19, 2022. No plants of *Heliopsis* 'Touch of Blush' have been offered for sale or sold in this country or anywhere in the world and such sale or disclosure within one year was either received directly or indirectly from the inventor.

BACKGROUND AND ORIGIN OF THE PLANT

The present invention relates to a new and distinct cultivar of *Heliopsis* 'Touch of Blush'. The new plant was selected as a single seedling from the progeny of a cross by the inventor between the proprietary hybrid known only by the breeder code 16-1-1 (not patented) as the female or seed parent and the proprietary hybrid known only by the breeder code 16-11-1 (not patented) as the male or pollen parent on Jul. 9, 2017 in Zeeland, Michigan. The seed was harvested in the fall of 2017 and the individual selected seedling eventually assigned the breeder code 17-10-1 toward the end of the trial period. 'Touch of Blush' was approved in a final evaluation in the summer of 2019 and slated for later introduction. The new plant was selected based on its compact habit, strong stems, ability to withstand lodging, mildew resistance, attractive colorful foliage, high-quality flowers over a long period, and ability to attract pollinators. The new plant has been asexually first propagated by division and later by shoot tip cuttings in Zeeland, Michigan with the resultant asexually propagated plants remaining identical to the original plant, stable and true to type in successive generations.

SUMMARY OF THE INVENTION

Plants of the new False Sunflower have not been observed under all possible combinations of environmental conditions and cultural practices. The phenotype may vary somewhat with variations in environmental conditions comprising temperature, daylength, light intensity, and fertility, without, however, any variations in genotype.

The following traits have been repeatedly observed and are determined to be the unique characteristics of the new *Heliopsis* plant. These characteristics in combination distinguish 'Touch of Blush' as a new and distinct *Heliopsis* plant:

1. Foliage with green directly surrounding the veins and near white between the veins;
2. Young foliage shows a blush of purplish-red;
3. Dense rounded mound plant habit;
4. Extensive branching habit with dark stems;
5. Freely flowering habit beginning in early summer and continuing for about six weeks;
6. Large inflorescences with single row of golden-yellow ray florets and dark brownish center disk florets;
7. Ray florets held above slightly outwardly to upwardly;
8. Strong garden performance.

The female parent has a taller habit with similar variegated foliage. The male parent has multiple rows of ray florets per inflorescence.

The following cultivars are the most similar cultivars known to the inventor: 'Bit of Honey' U.S. Plant Pat. No. 35,063, 'Loraine Sunshine' U.S. Plant Pat. No. 10,690, 'Summer Green' U.S. Plant Pat. No. 23,410, 'Sunstruck' U.S. Plant Pat. No. 25,524, 'Double Sunstruck' U.S. Plant Pat. No. 26,608, and 'Summer Pink' U.S. Plant Pat. No. 23,390.

'Bit of Honey' has multiple rows of ray florets per inflorescence. 'Loraine Sunshine', 'Summer Green', and the seed variety 'Sunburst' (not patented) are all taller and more upright in habit but have similar variegated foliage. 'Sunstruck' has a shorter more compact habit with similar variegated foliage. 'Double Sunstruck' has more ray florets, weaker stems that have a greater tendency to lodge. None of the above cultivars have the dark stems and the reddish-purple foliage blush. 'Summer Pink' has variegated foliage that is strongly cupped, but has a moderate rosy blush.

BRIEF DESCRIPTION OF THE DRAWINGS

The photographs of the new plant demonstrate the unique traits of *Heliopsis* 'Touch of Blush' and the overall appearance of a two-year-old plant in the full sun display garden of a nursery in Zeeland, Michigan. The colors are as accurate as reasonably possible with color reproductions. Changes in ambient light spectrum, source, and direction may cause the appearance of minor variations in color.

DETAILED BOTANICAL DESCRIPTION

Figure 1:
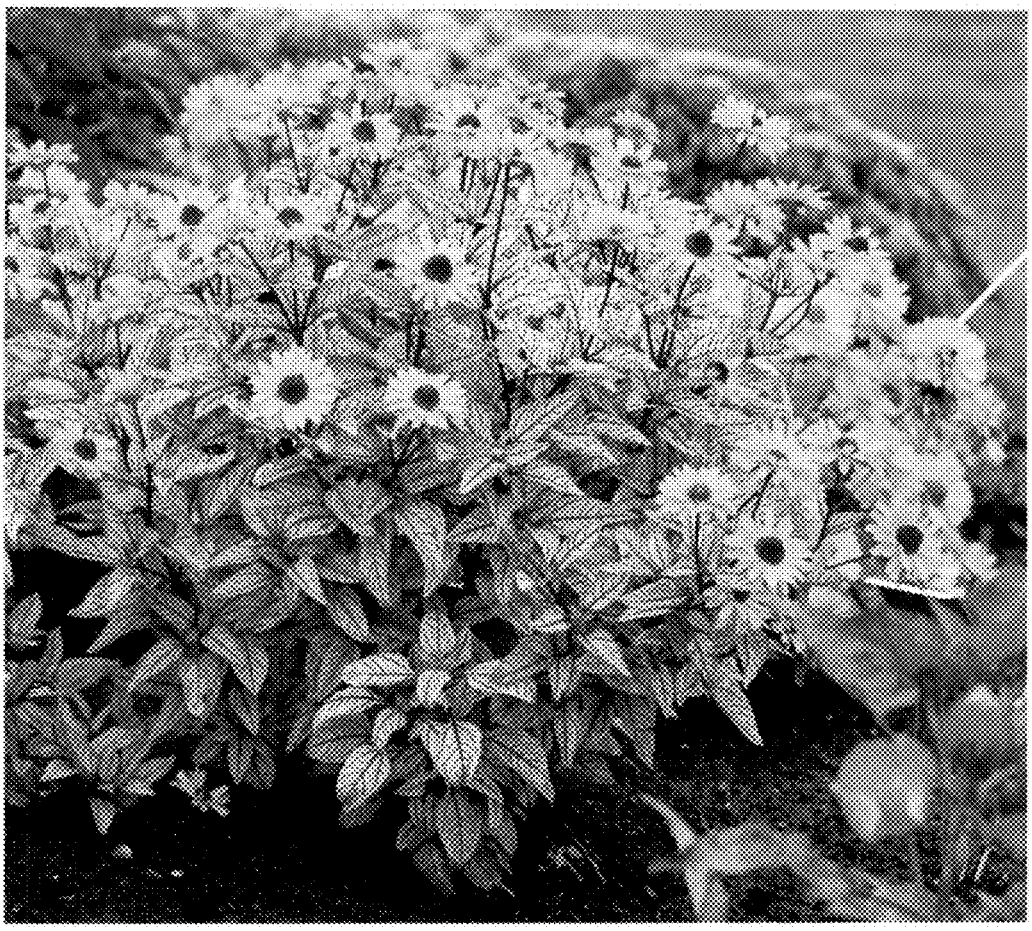
FIG. 1 shows the landscape habit of the new plant in mid-season flowering.
Figure 2:
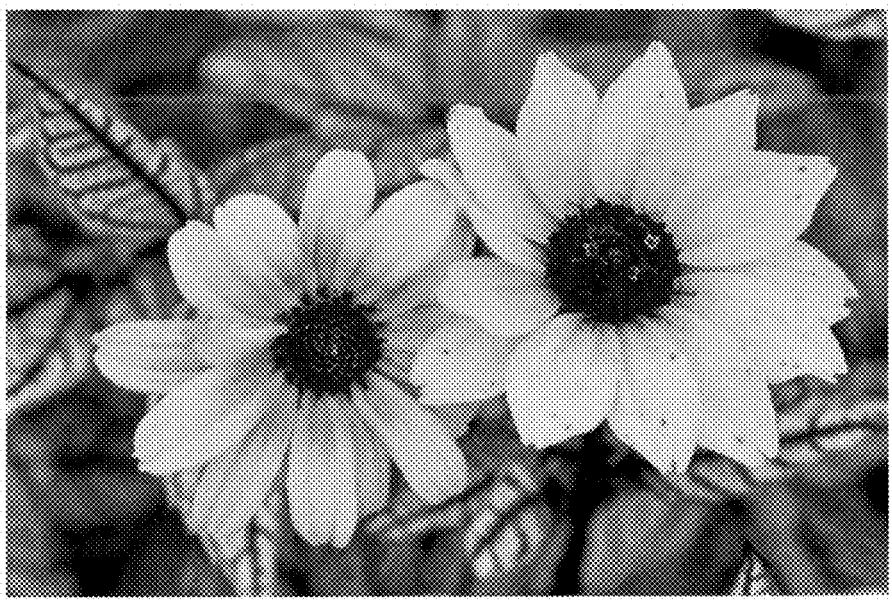
FIG. 2 shows a close-up of two inflorescences from above at different maturity stages.
Figure 3:
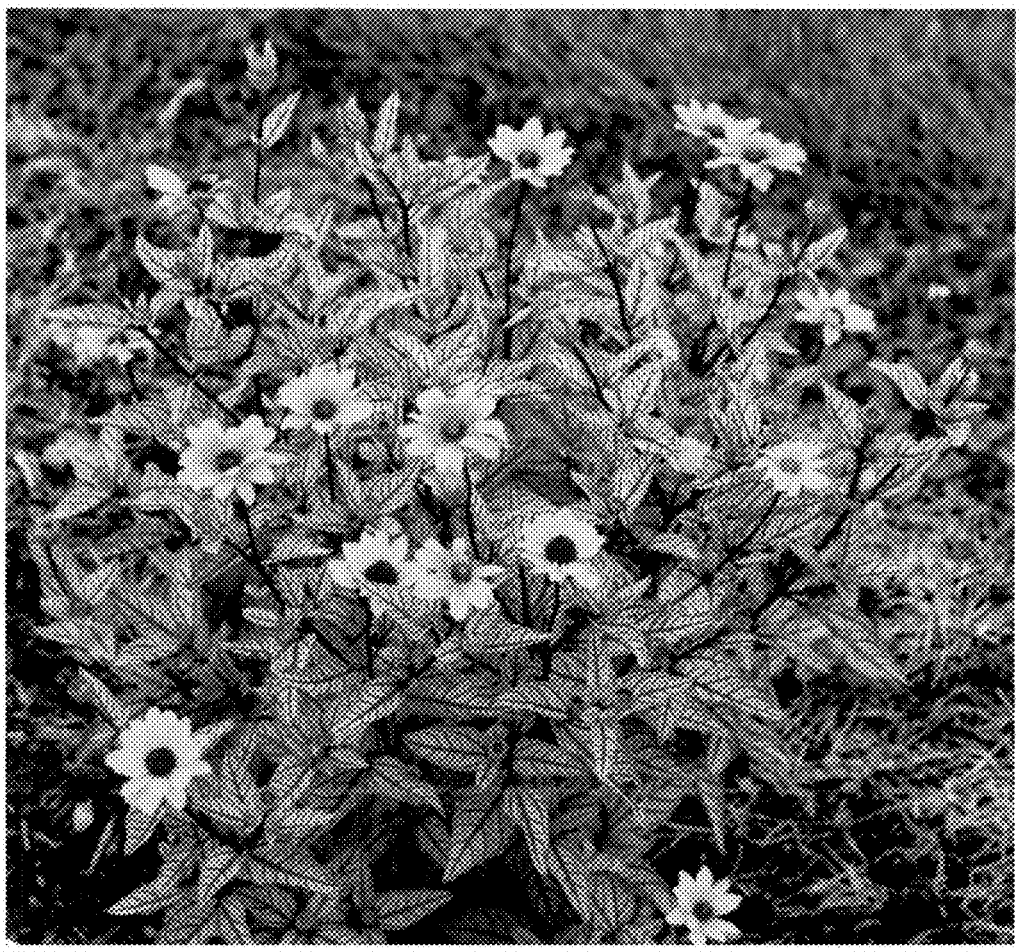
FIG. 3 shows the new plant in the early flowering with reddish-purple blush on the foliage.

The following descriptions and color references are based on the 2015 edition of The Royal Horticultural Society Colour Chart except where common dictionary terms are used. *Heliopsis* 'Touch of Blush' has not been observed under all possible environments. The phenotype may vary slightly with different growing environments such as temperature, light, fertility, soil pH, moisture, and maturity levels, but without any change in the genotype. The following observations and size descriptions are based on three-year-old plants grown in a trial garden and a partially shaded greenhouse at a nursery in Zeeland, Michigan with supplemental fertilizer and water as needed and without growth regulators or pinching.

Botanical classification: *Heliopsis helianthoides;*

Parentage: The female (seed) parent is 16-1-1; the male (pollen) parent is 16-11-1;

Plant habit: Multi-stemmed, heavily-branched, herbaceous perennial forming a dense rounded mound;

Propagation: Shoot tip cuttings;

Plant size: To about 45 cm tall and 50 cm wide;

Time to initiate roots: About one to two weeks;

Growth rate: Moderate; about 8 to 12 weeks to finish in a 3.8-liter container from a rooted 25 mm plug liner;

Root description: Fibrous; medium thickness; light tan to white in color, depending on soil composition, water quality, fertilizer type and formulation, substrate temperature, and physiological age of roots; medium density;

Stems: To about 12 per plant; cylindrical; micro-puberulent; to about 40 cm length and 6 mm diameter at base;

Stem color: Between RHS N186A and RHS N186B;

Branches: About 5 branches per stem beginning about 15 cm above soil; cylindrical; micro-puberulent; strong; flexible; length to about 24 cm; width to about 4 mm across at base;

Branch aspect: About 45 degrees above horizontal;

Nodes: About 7 below branches and a total of 12 to 16 before inflorescences; internode length average 1.6 cm;

Node color: Between RHS 162C with a variable blush of nearest RHS N186B;

Leaf description: Narrowly ovate to broadly lanceolate; opposite; apex acute; base obtuse to truncate; margin serrate with 12 to 14 teeth per side; scaberulose adaxial and abaxial;

Leaf size: To about 8 cm long and 4 cm wide, average about 6 cm long and 3 cm wide;

Leaf color: Young expanding adaxial nearest RHS 13D between veins, the area directly surrounding veins nearest RHS 137A, and with a light blush concentrated near the margin of nearest RHS N79C; young expanding abaxial nearest RHS 13D between veins, the area directly surrounding veins between RHS 138A and RHS 137C with a light blush concentrated near the margin of nearest RHS N79C; mature adaxial between RHS NN155C and RHS NN155B between the veins with portion directly surrounding veins nearest RHS 137A, mature abaxial between RHS NN155A and RHS NN155B between the veins with portion directly surrounding veins nearest RHS 137A;

Veins: Reticulate; slightly recessed and glabrous adaxial, abaxial micro-puberulent and costate;

Vein color: Young adaxial between RHS 145A and RHS 146D, abaxial nearest RHS 148C; mature adaxial nearest RHS N148C and abaxial nearest RHS 146D;

Petioles: Concavo-convex; sparsely puberulent adaxial and abaxial; to about 14 mm long and 2 mm across;

Petiole color: Adaxial center nearest RHS N186C, margin RHS 146D with a moderate blush of nearest RHS N186C; abaxial center nearest RHS N186C, margin RHS 146D with a moderate blush of nearest RHS N186C;

Inflorescence: In terminal capitulum; initial inflorescences semi-double with disk florets in the center and two to three layers of ray florets, later inflorescences nearly single with a single layer of imbricate ray florets; about 75 to 100 inflorescences per plant;

Flowering season: Beginning early July and continuing for about six weeks;

Inflorescence buds: Tubular with flat top and rounded base; with ray florets still upright about 20 mm tall and 16 mm across;

Bud color: Ray florets adaxial nearest RHS 22A, abaxial variable with nearest RHS 21B with a slight undertone of nearest RHS 151D and between RHS 152B and RHS N199C;

Inflorescence longevity: Lasting about seven to ten days on the plant or as a cut flower; persistent;

Fragrance: Very slight, sweet;

Inflorescence size: To about 5.5 cm across and 3 cm tall;

Disk receptacle: Flattened round shape, about 7 mm across and 6 mm tall;

Receptacle color: Nearest RHS 146C;

*Ray florets*.—Ligulate; between 14 and 28 per inflorescence, arranged in about 1 or 2 imbricate whorls; typically larger number of ray florets on the primary terminal inflorescence; lanceolate with bifid emarginate apex, indented to about 2 mm; base attenuate to cuneate; margin entire; adaxial and abaxial surface glabrous and matte; aspect horizontal when mature; with typically two longitudinal furrows.

*Size*.—To about 18 mm long and 9 mm across near middle.

*Ray floret color*.—Upon initially becoming flat — adaxial proximal one-third between RHS N25A and RHS N25B and distal portion between RHS 21B and RHS 23B; abaxial nearest RHS 21C; near the final stage of effective inflorescence adaxial between RHS 21B and RHS 21C, abaxial nearest 21D.

*Disk florets*.—Prefect; about 80 per inflorescence and arrangement in typical Fibonacci spirals; tubular with exserted anthers and style.

*Size*.—To about 8 mm long and 3 mm wide at expanded style.

*Corolla tube*.—Consisting of five tepals; to about 6 mm long and 2 mm wide at apex.

*Tepals*.—Five; acute apex; fused in basal 5 mm; margin entire; glabrous; slightly lustrous both adaxial and abaxial; to about 5 mm long and about 0.7 mm across at fusion; color apex adaxial and abaxial nearest RHS 23B when first open and maturing to nearest RHS 178B; proximal adaxial portion nearest RHS 145D, proximal portion abaxial between RHS N144D and RHS 145C.

Reproductive organs: Ray florets anandrous;

*Gynoecium*.—To 9 mm long; exserted.

*Style*.—Cylindrical; to about 4 mm long and 0.2 mm diameter; color nearest RHS N186C.

*Stigma*.—Bifid in distal 1.5 mm; color nearest RHS N186C.

*Ovary*.—3 mm long and 1 mm across; color nearest 157A.

Reproductive organs: Disk florets: perfect;

*Gynoecium*.—To 9 mm long; exserted.

*Style*.—Cylindrical; to about 4 mm long and 0.2 mm diameter; color nearest RHS N186C.

*Stigma*.—Bifid in distal 2 mm; color nearest RHS N186C.

*Ovary*.—3 mm long and 1 mm across; color nearest 157A.

*Androecium*.—Connate; to about 3 mm long.

*Anthers*.—Five; synandrous; introrse; basifixed; tube to about 2.5 mm long and 0.7 mm diameter; color nearest RHS 200B.

*Filaments*.—Five; to about 2 mm long and 0.2 mm diameter; color nearest RHS 155C.

*Pollen*.—Abundant; color nearest RHS 17A.

Seeds: Achene; truncate apex; acute base; surface smooth, glabrous, matte; quadrangular distally; to about 4 mm long and 2 mm across at apex, average about 3 mm long and 1.8 mm across; about 63 per inflorescence; color nearest RHS 200A;

Flowering period: In Western Michigan beginning in early July for about six weeks; individual florets remain open for about 4 to 6 days;

Flower attitude: Upwardly to slightly outwardly;

Phyllaries: About 27 per inflorescence in two whorls; lanceolate; acute apex; margin entire; puberulent and matte adaxial and abaxial; about 8 mm long and 2 mm across at base;

Phyllary color: Adaxial between RHS N137A and RHS 137A; abaxial nearest RHS 146A;

Peduncles: Cylindrical; micro-puberulent; strong; stiff; upright; to about 10.8 cm long, 2.5 mm diameter proximally and 6.0 mm diameter at base of inflorescence;

Peduncle color: Nearest RHS 146D;

Growth: The new plant has been observed to have good garden performance and tolerance to high winds and strong rains.

Hardiness: Winter hardy in USDA zones 4 to 9;

Pest and disease susceptibility: Shows resistance to powdery mildew (*Neoerysiphe galeopsidis*) but shows no other resistance or susceptibility observed beyond that which is typical for *Heliopsis*.

I claim:

1. A new and distinct hardy perennial *Heliopsis* plant named 'Touch of Blush' essentially as herein described and illustrated.

* * * * *